United States Patent [19]

Carroll et al.

[11] Patent Number: 4,967,747
[45] Date of Patent: Nov. 6, 1990

[54] IMPLANTABLE CARDIAC DEFIBRILLATOR EMPLOYING A SWITCHED CAPACITOR GAIN/FILTER STAGE HAVING A TRANSIENT-FREE GAIN CHANGE

[75] Inventors: Kenneth J. Carroll, San Jose; Benjamin D. Pless, Menlo Park, both of Calif.

[73] Assignee: Ventritex, Inc., Sunnyvale, Calif.

[21] Appl. No.: 353,952

[22] Filed: May 19, 1989

[51] Int. Cl.$^5$ .............................................. A61N 1/00
[52] U.S. Cl. ............................................... 128/419 D
[58] Field of Search ........ 128/419 D, 419 PG, 419 P, 128/419 PS

[56] References Cited

U.S. PATENT DOCUMENTS

| | | | |
|---|---|---|---|
| 4,168,711 | 9/1979 | Cannon et al. | 128/419 D |
| 4,328,808 | 5/1982 | Charbonnier | 128/419 D |
| 4,375,817 | 3/1983 | Engle | 128/419 D |
| 4,693,253 | 9/1987 | Adams | 128/419 D |
| 4,800,883 | 1/1989 | Winstrom | 128/419 D |

OTHER PUBLICATIONS

"High-Resolution Switched-Capacitor D/A Converter", Gregorian, Microelectronics Journal, vol. 12, No. 2, 1981, pp. 10-13.

Primary Examiner—Francis Jaworski
Assistant Examiner—George Manuel
Attorney, Agent, or Firm—Gerstman & Ellis, Ltd.

[57] ABSTRACT

An implantable cardiac defibrillator includes electrodes coupled to a patient's heart, sensing circuitry having inputs connected to the electrodes for sensing cardiac electrical signals, charging means for storing a charge, and discharge means for delivering a shock to the heart. The sensing circuitry includes switched capacitor gain/filter means for providing an output signal which is transient-free during a gain change operation and which maintains a constant filter bandwidth for each gain setting.

20 Claims, 3 Drawing Sheets

IMPLANTABLE CARDIAC DEFIBRILLATOR EMPLOYING A SWITCHED CAPACITOR GAIN/FILTER STAGE HAVING A TRANSIENT-FREE GAIN CHANGE

BACKGROUND OF THE INVENTION

This invention relates generally to implantable cardiac defibrillator devices for defibrillating the heart of a patient and more particularly, it relates to an implantable cardiac defibrillator employing improved sensing circuitry for processing ECG heart signals from the atrium and/or ventricle.

In recent years there has been substantial progress made in the research and development of defibrillating devices for providing an effective medical response to various disorders, such as ventricular fibrillation. Research effort has also been made toward developing improved sensing techniques for reliably monitoring heart activity so as to determine whether a defibrillating high energy shock is required.

However the implantable cardiac defibrillators of the prior art used comparatively simple sensing circuits. These prior art sensing circuits would typically include switched capacitor circuits. When it was desired to make a gain change, e.g., by switching in an additional capacitor, the output of the prior art switched capacitor circuits would experience a transient change referred to as a "glitch." For purposes of completeness, reference is made to an article entitled "High Resolution Switched Capacitor D/A Converter" by Roubik Gregorian in *Microelectronics Journal*, Vol. 12, No. 2, 1981, pp. 10–13. It would therefore be desirable to provide an implantable cardiac defibrillator employing improved sensing circuitry for processing ECG heart signals from the atrium and/or ventricle wherein the gain thereof may be changed without producing a transient or glitch on its output.

The present invention provides an implantable cardiac defibrillator employing a switched capacitor gain/filter stage whose gain can be changed without causing a transient on its output.

SUMMARY Of THE INVENTION

It is a general object of the present invention to provide an implantable cardiac defibrillator employing improved sensing circuitry for processing ECG heart signals from the atrium and/or ventricle.

Another object of the present invention is to provide an implantable cardiac defibrillator employing sensing circuitry formed of a switched capacitor gain/filler stage for providing an output signal which is transient-free during a gain change operation.

It is still another object of the present invention to provide an implantable cardiac defibrillator which includes sensing circuitry formed of a switched capacitor gain/filter stage wherein pole-compensating switching means maintains a constant pole frequency during a gain change operation.

It is still yet another object of the present invention to provide an implantable cardiac defibrillator which includes sensing circuitry formed of a switched capacitor gain/filter structure wherein any selectively switchable capacitors are precharged to essentially the same voltage as the associated nonselectively switchable capacitors in the circuit so that when they are switched into the gain/filter structure there will be little charge sharing between the capacitors and hence little in the way of an undesirable transient in the output of the gain/filter structure.

It is yet still another object of the present invention to provide an implantable cardiac defibrillator which includes means for switching in any selectively switchable capacitors in a switched capacitor gain/filter structure outside of a stage acquisition phase so that the resulting gain-changing operation will result in little in the way of an undesirable transient in the output.

In accordance with these aims and objectives, the present invention is concerned with the provision of an implantable cardiac defibrillator which includes electrodes, sensing circuitry, a charge storing device, and a discharging device. The electrodes are coupled to a patient's heart. The sensing circuitry is provided with inputs connected to the electrodes for sensing cardiac electrical signals. A charge is stored on the charge storing device. The discharging device is used to deliver a shock to the heart. The sensing circuitry includes switch capacitor gain/filter means for providing an output signal which is transient-free during a gain change operation.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein.

DESCRIPTION OF THE PREfERRED EMBODIMENT

Figure 1:
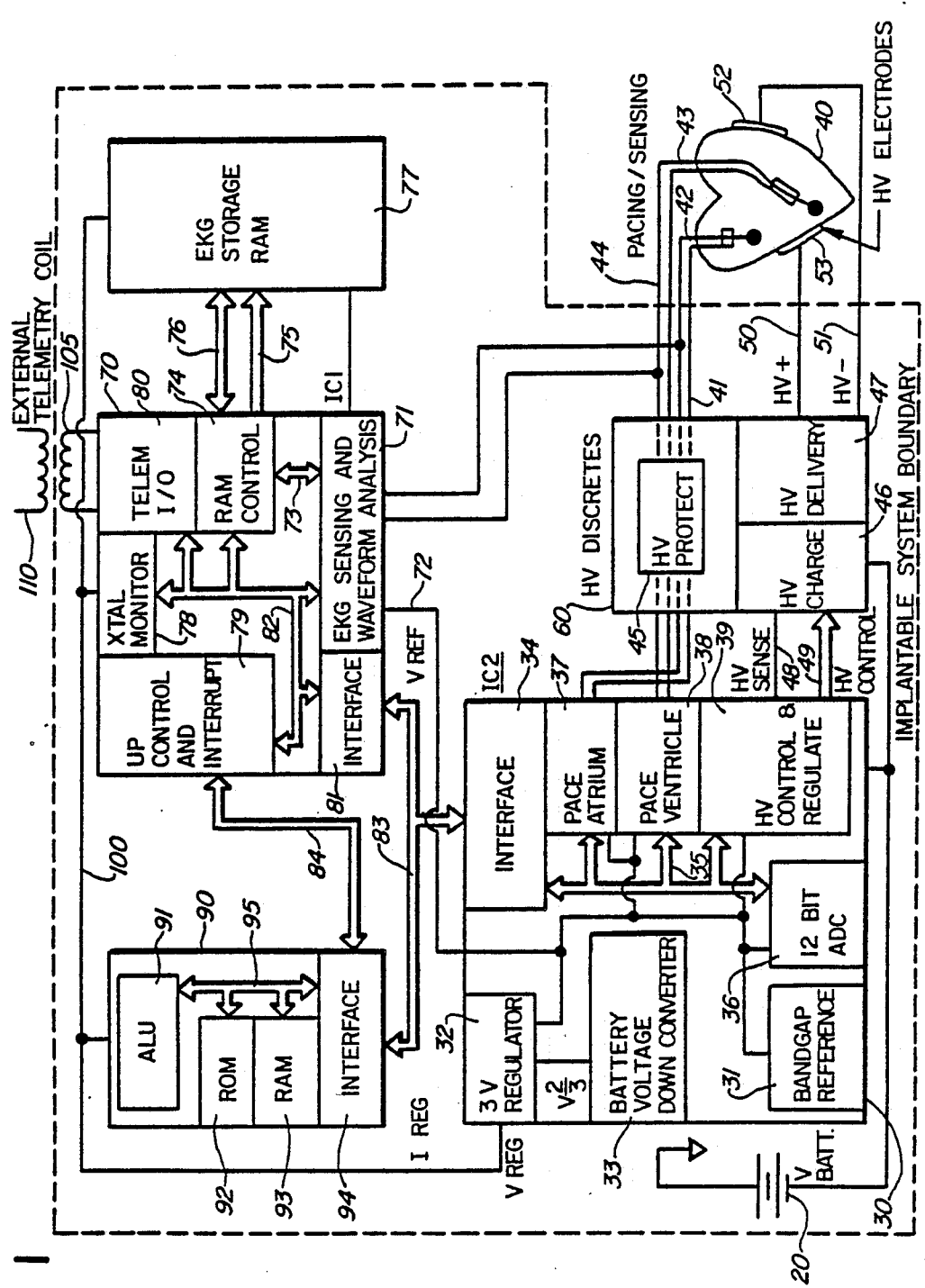
FIG. 1 is a block diagram of an implantable cardiac defibrillator, constructed in accordance with the principles of the present invention.

In FIG. 1, there is illustrated in a functional block diagram format the internal and external elements of an implantable cardiac defibrillator constructed in accordance with the principles of the present invention, A detailed description of the elements of FIG. 1 as well as their interconnection and operation has been presented in co-pending application Ser. No. 344,011, filed Apr. 26, 1989, entitled "Method for Cardiac Oefibrillation" and assigned to the same assignee as the present invention, which is hereby incorporated by reference. Thus, the detailed description will not herein be repeated. However, a general description of the elements of FIG. 1 required for an understanding of the present invention will be presented.

In particular, FIG. 1 shows an implantable cardiac defibrillator which includes four integrated circuit chips IC1–IC4 and a set of high voltage discrete component blocks 45–47. The block 45 contains high voltage protection circuits which prevent the atrium and ventricle pacing circuits 37 and 38 from being damaged by the defibrillation voltage. The block 46 is a high voltage charge block and contains a high voltage capacitor that is charged to deliver a defibrillating pulse. The defibrillating pulse is delivered from the high voltage delivery block 47 to electrodes 52 and 53 connected to the heart 40 via lines 50 and 51.

The chip IC1 contains an ECG sensing and waveform analysis block 71 which receives ECG heart signals to be monitored and processed. Specifically, the heart signals coming from the atrium are fed to the sensing and waveform analysis block 71 via the line 42. The heart signal coming from the ventricle is fed to the block 71 via the line 44.

The block 71 includes a first three-stage amplifier/filter network for sensing the heart signals in the atrium and a second three-stage amplifier/filter network for sensing the heart signals in the ventricle. A switched capacitor filter/gain stage utilized in the first network or second network is illustrated in detail in FIG. 2 for providing an output which is transient-free or "glitchless" during a gain change operation.

Figure 2:
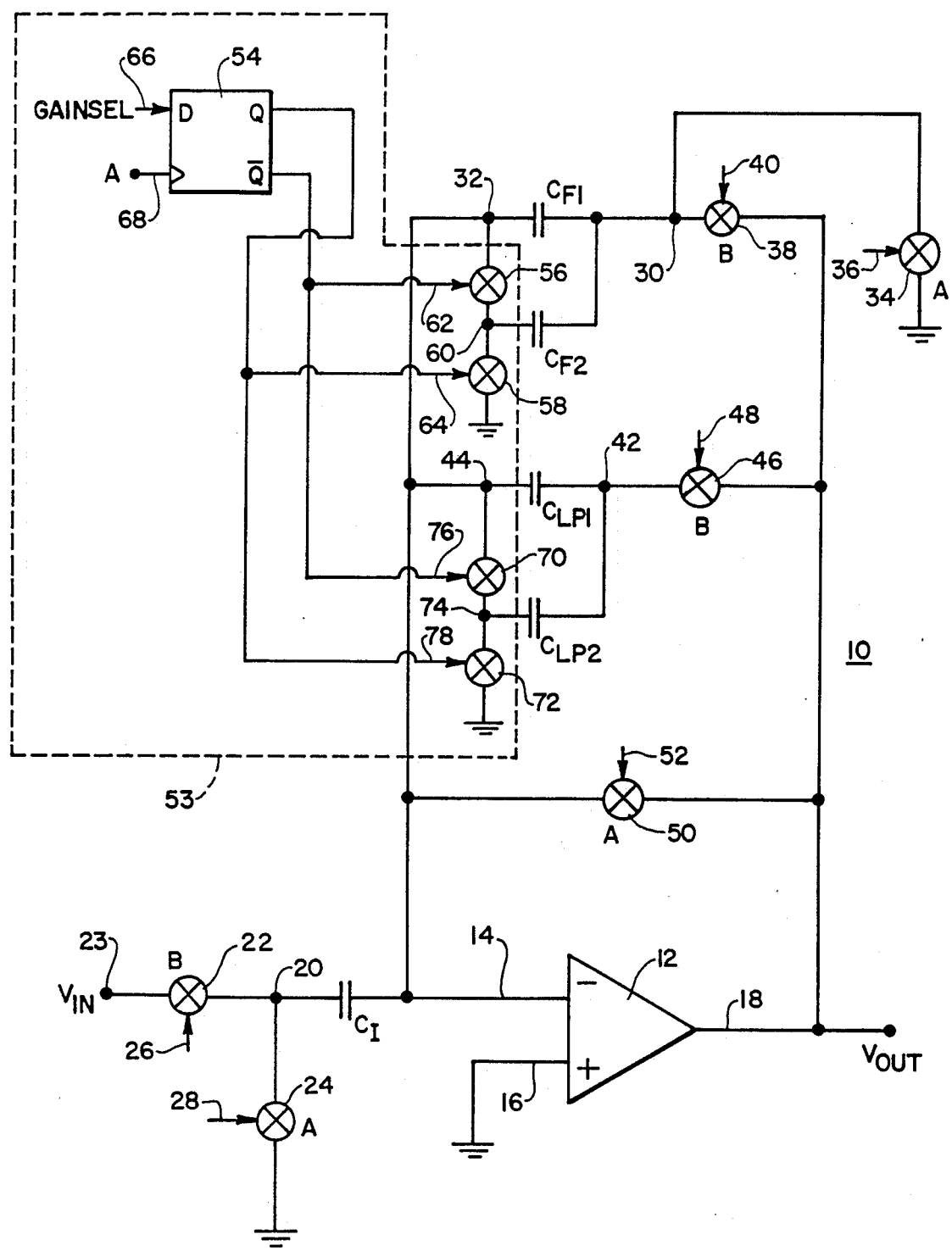
FIG. 2 is a schematic circuit diagram of a switched capacitor gain/filter stage, constructed in accordance with the principles of the present invention.

Referring now in detail to FIG. 2 of the drawings, there is illustrated a schematic circuit diagram of a switched capacitor gain/filter stage 10 constructed in accordance with the principles of the present invention. The switched capacitor stage 10 comprises an operational amplifier 12 which has an inverting input terminal 14, a non-inverting input terminal 16, and an output terminal 18. The non-inverting input terminal is connected to a reference voltage VREF shown here as a ground potential.

An input capacitor $C_I$ has its one end connected to the input terminal 14 of the operational amplifier. The other end of the input capacitor $C_I$ is connected to a node 20. A switch gate 22 has its signal input connected to receive an input signal or voltage $V_{in}$ via a signal input terminal 23 and its signal output connected to the node 20. A switch gate 24 has its signal input connected to the ground potential and its signal output connected to the node 20. The control terminal 26 of the switch gate 22 is connected to receive a control signal B, and the control terminal 28 of the switch gate 24 is connected to receive a control signal A.

A first feedback capacitor $C_{F1}$ has its one end connected to one end of a second feedback capacitor $C_{F2}$ at a node 30. The other end of the first feedback capacitor $C_{F1}$ is connected to a node 32 and to the input terminal 14 of the operational amplifier. A switch gate 34 has its signal input connected to the ground potential, its signal output connected to the node 30, and its control terminal 36 connected to receive the control signal A. A switch gate 38 has its signal input connected to the node 30, its signal output connected to the output terminal 18 of the operational amplifier, and its control terminal 40 connected to receive the control signal B.

A first filter capacitor $C_{LP1}$ has its one end connected to one end of a second filter capacitor $C_{LP2}$ at a node 42. The other end of the first filter capacitor $C_{LP1}$ is connected to a node 44 and to the input terminal 14. A switch gate 46 has its signal input connected to the node 42, its signal output connected to the output terminal 18, and its control terminal 48 connected to receive the control signal B. A switch gate 50 has its signal input connected to the output terminal 18 of the operational amplifier and its signal output connected to the input terminal 14. The control terminal 52 of the switch gate 50 is connected to receive the control signal A.

In order to change the gain, there is provided a gain select controller 53 consisting of a D-type flip-flop 54 and a pair of gain switch gates 56 and 58 for selectively switching in and out the second feedback capacitor $C_{F2}$. The switch gate 56 has it signal input connected to a node 60 and the other end of the second feedback capacitor $C_{F2}$. The signal output of the switch gate 56 is connected to the node 32 and the other end of the first feedback capacitor $C_{F1}$. The switch gate 58 has its signal input connected to the ground potential and its signal output connected to the node 60.

The switch gate 56 has a control terminal 62 which is connected to receive a complement gain control signal at the $\overline{Q}$ output of the flip-flop 54. The switch gate 58 has a control terminal 64 which is connected to receive a true gain control signal at the Q output of the flip-flop. The flip-flop 54 receives a gain select signal GAINSEL on its D-input terminal on line 66 and the control signal A on its clock input terminal on line 68 for generating the respective true and complement gain control signals at the Q and $\overline{Q}$ outputs.

In order to insure that the pole frequency does not move due to the gain change operation, the gain select controller 53 further includes a pair of pole-compensating switch gates 70 and 72 for selectively switching in and out the second filter capacitor $C_{LP2}$. This second filter capacitor $C_{LP2}$ is switched in and out with the first filter capacitor $C_{LP1}$ at the same time the second feedback capacitor $C_{F2}$ is being switched in and out with the first feedback capacitor $C_{F1}$. The switch gate 70 has a signal input connected to a node 74 and to the other end of the second filter capacitor $C_{LP2}$. The signal output of the switch gate 70 is connected to the node 44 and to the other end of the first filter capacitor $C_{LP1}$. The switch gate 72 has its signal input connected to the ground potential and its signal output connected to the node 74.

The pole-compensating switch gate 70 has a control terminal 76 which is connected to receive the same complement gain control signal at the $\overline{Q}$ output which was sent to the control terminal 62 of the gain switch gate 56. Similarly, the pole-compensating switch gate 72 has a control terminal 78 which is connected to receive the same true gain control signal at the Q output, which was sent to the control terminal 64 of the gain switch gate 58.

Figure 3:
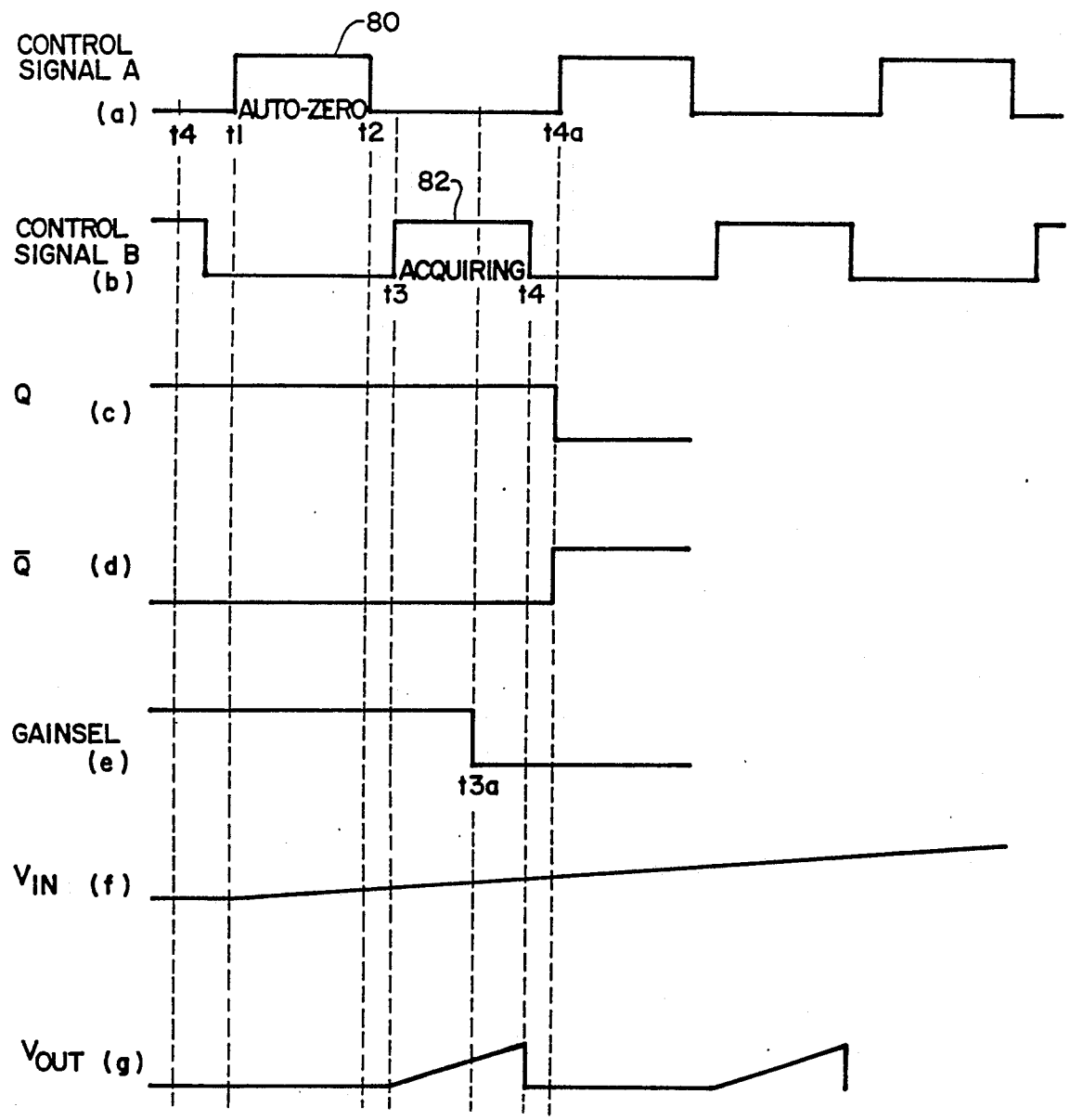
FIG. 3(a) to 3(g) are waveforms useful in understanding the operation of the switched capacitor stage of FIG. 1.

FIG. 3(a) illustrates a waveform 80 which represents the control signal A that is applied to the control terminals of the respective switch gates 24, 34 and 50. When the control signal A is active or at the logic "1" level such as between the times t1 and t2, this is generally referred to as the "auto-zero" phase. FIG. 3(b) illustrates a waveform B2 which represents the control signal B that is applied to the control terminals of the respective switch gates 22, 38 and 46. When the control signal B is active or at the logic "1" level, such as between the times t3 and t4, this is generally referred to as the "acquiring" phase. It will be noted that the auto-zero phase of the control signal A and the acquiring phase of the control signal B are non-overlapping and operate in what is known as a break-before-make fashion. In other words, the auto-zero phase will make a high-to-low transition prior to the time when the acquiring phase makes a low-to-high transition. It should be apparent to those skilled in the art that the control signals A and B may be generated from a conventional non-overlapping clock generator (not shown).

During the auto-zero phase, the control signal A is at a high or logic "1" level and the control signal B is at a low or "0" level. A signal applied to the signal input of switch gates 24, 36 and 50 during the auto-zero phase will be coupled to the signal output. Thus, the switch gates 24, 36 and 50 are defined to be closed or turned on. However, a signal applied to the signal input of the switch gates 22, 38 and 46 during the auto-zero phase will not be coupled to the signal output. Therefore, the switch gates 22, 38 and 46 are defined to be open or turned off.

Similarly, during the acquiring phase the control signal B is at a high logic level and a control signal A is at a low logic level. A signal applied to the signal input of the switch gates 22, 38 and 46 during the acquiring phase will be coupled to the signal output. Thus, the switch gates 22, 38 and 46 are defined to be closed or turned on. However, a signal applied to the signal input of the switch gates 24, 36 and 50 during the acquiring phase will not be coupled to the signal output. Therefore, the switch gates 24, 36 and 50 are defined to be opened or turned off.

The operation of the switched capacitor gain/filter stage 10 of FIG. 2 will now be explained with reference to the waveform diagrams of FIGS. 3(a)–3(g). Initially, it will be assumed that at the time t0 that the gain select signal GAINSEL on the line 66 is at a logic "1" level. Further, the Q output of the flip-flop 54 is assumed to be at the logic "1" level, and the $\bar{Q}$ output is at the logic "0" level. Since the control terminals of the switch gates 58 and 72 are connected to the Q output, the switch gates 58 and 72 are closed. Since the control terminals of switch gate 62 and 70 are connected to the $\bar{Q}$ output, the switch gates 62 and 70 are opened.

At the time t0, the node 60 connected to the "top" plate of the second feedback capacitor $C_{F2}$ is tied to the ground potential via the switch gate 58. Since the node 32 connected to the "top" plate of the first feedback capacitor $C_{F1}$ is also tied to the inverting input of the operational amplifier which is a "virtual" ground, the top plates of the feedback capacitors $C_{F1}$ and $C_{F2}$ are at the same potential. Further, the "bottom" plates of the feedback capacitors $C_{F1}$ and $C_{F2}$ are also at the same potential due to their common connection at the node 30. Similarly, the node 74 connected to the "top" plate of the second filter capacitor $C_{LP2}$ is tied to the ground potential via the switch gate 72. Since the node 74 connected to the "top" plate of the first filter capacitor $C_{LP1}$ is also tied to the ground potential, the top plates of the capacitors $C_{LP1}$ and $C_{LP2}$ are at the same potential. The bottom plates of the capacitors $C_{LP1}$ and $C_{LP2}$ are likewise at the same potential due to their common connection at the node 42.

During the auto-zero phase between the times t1 and t2, the common node 30 is selectively disconnected from the output terminal 18 of the operational amplifier and is tied to the ground potential via the switch gate 34 so as to permit discharging of the first and second feedback capacitors. The common node 42 is also disconnected from the output terminal during the auto-zero phase, but the charge on the capacitor $C_{LP1}$ is "held" creating the overall filtering function. The capacitor $C_{LP2}$ due to its common connection at the node 42 and its top plate connection to ground, which is the "ideal" voltage at the top plate of the capacitor $C_{LP1}$, remains charged to the same voltage as the capacitor $C_{LP1}$. It will be noted that the inverting input terminal 14 and the output terminal 18 of the operational amplifier are shorted together during this auto-zero phase. During the acquiring phase between the times t3 and t4, the common node 30 is connected to the output terminal 18. This provides an output voltage $V_{out}$ on the output terminal 18 with a gain of $C_I/C_{F1}$.

It will now be assumed that at the time t3a it is desired to make a gain change by adding the second feedback capacitor $C_{F2}$ in parallel with the first feedback capacitor $C_{F1}$. If the gain change were permitted to take place during the time t3a of the acquiring phase any displacement of charge between the capacitors $C_{F1}$ and $C_{F2}$ due to the fact that node 32 and the input terminal 14 sit at the stage input offset voltage while the signal input to switch 58 sits at the ground potential and due to a transient induced shift in the voltage at the input terminal 14 at the beginning of the acquiring phase would appear as a glitch in the output voltage at the output terminal 18 since the switch gate 38 would be closed. The "transient-free" gain change is promoted by two factors; (1) that the capacitors $C_{F2}$ and $C_{LP2}$ are held at essentially the same potential as the capacitors $C_{F1}$ and $C_{LP1}$, and (2) the gain change is synchronized to change only during the auto-zero phase. In other words, the gain change is not allowed to happen until the time t4a of the auto-zero phase where the common node 30 has already been disconnected from the output terminal 18.

The gain select signal GAINSEL illustrated in FIG. 3(e) makes a high-to-low transition at the time t3a indicating a desired gain change. However, the true and complement gain control signals, illustrated in FIGS. 3(c) and 3(d), do not change until the time t4a when the control signal A makes a low-to-high transition. It should be apparent to those skilled in the art that no significant displacement of charge actually occurs between the feedback capacitors $C_{F1}$ and $C_{F2}$ since they are discharged to ground during the auto-zero phase. It will also be noted that the top plate of the second feedback capacitor $C_{F2}$ is being switched between the same potentials, e.g., the ground potential and a virtual ground. Consequently, the gain has been changed without a glitch in the output signal on the output terminal 18 at the time t4a to have a new and lower gain of $C_I/(C_{F1}+C_{F2})$. The input signal $V_{in}$ is illustrated in FIG. 3(f), and the output voltage $V_{out}$ is illustrated in FIG. 3(g).

In order to insure that the pole frequency does not change or move due to the gain change (adding of the second feedback capacitor $C_{F2}$), the second filter capacitor $C_{LP2}$ is also connected in parallel with the first filter capacitor $C_{LP1}$ at the same time t4a. As can be seen, the switch gate 72 will be opened and the switch gate 70 will be closed. It will also be noted that the top plate of the second filter capacitor $C_{LP2}$ is being switched between essentially the same potentials. Again, any displacement of charge between the capacitors $C_{LP1}$ and $C_{LP2}$ will not be seen by the output terminal since the common node 42 will be disconnected from the output terminal during the auto-zero phase. Therefore, the addition of the pole-compensating capacitor $C_{LP2}$ is also synchronized with the auto-zero phase and will also not cause a glitch to appear in the output voltage $V_{out}$ on the output terminal 18.

From the foregoing detailed description, it can thus be seen that the present invention provides an implantable cardiac defibrillator which employs improved sensing circuitry for processing ECG heart signals from the atrium and/or ventricle. The sensing circuitry includes a switched capacitor gain/filter stage for providing an output signal which is transient-free or "glitchless" during a gain change operation.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. An implantable cardiac defibrillator comprising:
   electrode means adapted to be coupled to a patient's heart;
   sensing means having inputs connected to said electrode means for sensing cardiac electrical signals
   means coupled to said electrode means for storing a charge;
   discharging means for delivering a shock to the heart; and
   said sensing means including switched capacitor gain/filter means for providing an output signal which is transient-free during a gain change operation.

2. An implantable cardiac defibrillator as claimed in claim 1, wherein said switched capacitor gain/filter means comprises amplifying means having an input and an output, first feedback means coupled between said input and said output of said amplifying means, second feedback means being selectably connected and disconnected to said first feedback means to provide a gain change, and gain switch means for selectably controlling the connecting and disconnecting of said second feedback means so as to prevent causing the transient on said output of said amplifying means.

3. An implantable cardiac defibrillator as claimed in claim 2, wherein said amplifying means comprises operational amplifier means having an inverting input terminal, a non-inverting input terminal and an output terminal.

4. An implantable cardiac defibrillator as claimed in claim 2, wherein said first feedback means comprises first capacitor means.

5. An implantable cardiac defibrillator as claimed in claim 4, wherein said second feedback means comprises second capacitor means.

6. An implantable cardiac defibrillator as claimed in claim 2, further comprising controlled switch means for disconnecting said first and second feedback means from said output of said amplifier means during a gain change.

7. An implantable cardiac defibrillator as claimed in claim 6, wherein said gain switch means and said controlled switch means are activated by different control signals for producing a two-phase operation thereof.

8. An implantable cardiac defibrillator as claimed in claim 7, wherein in a first phase said first and second feedback means are connected to said output of said amplifier means and said gain switch means is prevented from switching the gain, and wherein in a second phase said first and second feedback means are disconnected from said output of said amplifier means to enable said gain switch means to switch the gain.

9. An implantable cardiac defibrillator as claimed in claim 2, further comprising input means for providing an input signal to said input of said amplifying means.

10. An implantable cardiac defibrillator comprising:
    electrode means adapted to be coupled to a patient's heart;
    sensing means having inputs connected to said electrode means for sensing cardiac electrical signals;
    means coupled to said electrode means for storing a charge;
    discharging means for delivering a shock to the heart;
    said sensing means including switched capacitor gain/filter means for providing an output signal which is transient-free during a gain change operation; and
    said switched capacitor gain/filter means having pole-compensating switching means for maintaining a constant pole frequency during the gain change.

11. An implantable cardiac defibrillator as claimed in claim 10, wherein said switched capacitor gain/filter means comprises amplifying means having an input and an output, first feedback means coupled between said input and said output of said amplifying means, second feedback means being selectably connected and disconnected to said first feedback means to provide a gain change, and gain switch means for selectably controlling the connecting and disconnecting of said second feedback means so as to prevent causing the transient on said output of said amplifying means.

12. An implantable cardiac defibrillator as claimed in claim 11, wherein said amplifying means comprises operational amplifier means having an inverting input terminal, a non-inverting input terminal and an output terminal.

13. An implantable cardiac defibrillator as claimed in claim 11, wherein said first feedback means comprises first capacitor means.

14. An implantable cardiac defibrillator as claimed in claim 13, wherein said second feedback means comprises second capacitor means.

15. An implantable cardiac defibrillator as claimed in claim 11, further comprising controlled switch means for disconnecting said first and second feedback means from said output of said amplifier means during a gain change.

16. An implantable cardiac defibrillator as claimed in claim 15, wherein said gain switch means and said controlled switch means are activated by different control signals for producing a two-phase operation thereof.

17. An implantable cardiac defibrillator as claimed in claim 16, wherein in a first phase said first and second feedback means are connected to said output of said amplifier means and said gain switch means is prevented from switching the gain, and wherein in a second phase said first and second feedback means are disconnected from said output of said amplifier means to enable said gain switch means to switch the gain.

18. An implantable cardiac defibrillator as claimed in claim 11, further comprising input means for providing an input signal to said input of said amplifying means.

19. An implantable cardiac defibrillator comprising:
    electrode means adapted to be coupled to a patient's heart;
    sensing means having inputs connected to said electrode means for sensing cardiac electrical signals;
    means coupled to said electrode means for storing a charge;
    discharging means for delivering a shock to the heart; and
    said sensing means including amplifying means having an input and an output and gain switch means responsive to a control signal for varying the gain between the input and the output of said amplifying means so as to provide an output signal which is transient-free during a gain change operation.

20. An implantable cardiac defibrillator as claimed in claim 19, wherein said amplifying means comprises operational amplifier means having an inverting input terminal, a non-inverting input terminal and an output terminal.

* * * * *